(12) United States Patent
Jones et al.

(10) Patent No.: US 8,795,373 B2
(45) Date of Patent: *Aug. 5, 2014

(54) INTERBODY FUSION DEVICE, INTEGRAL RETENTION DEVICE, AND ASSOCIATED METHODS

(75) Inventors: Robert J. Jones, Austin, TX (US); Mark Rahm, Temple, TX (US); Kevin Dunworth, Dripping Springs, TX (US)

(73) Assignee: SpineSmith Partners, L.P., Austin, TX (US)

( * ) Notice: Subject to any disclaimer, the term of this patent is extended or adjusted under 35 U.S.C. 154(b) by 404 days.

This patent is subject to a terminal disclaimer.

(21) Appl. No.: 12/018,703

(22) Filed: Jan. 23, 2008

(65) Prior Publication Data

US 2009/0105830 A1    Apr. 23, 2009

Related U.S. Application Data

(60) Provisional application No. 60/981,414, filed on Oct. 19, 2007.

(51) Int. Cl.
*A61F 2/44*    (2006.01)

(52) U.S. Cl.
USPC ............. 623/17.16; 623/17.11; 606/296

(58) Field of Classification Search
USPC ........... 623/17.11–17.16; 606/246, 279, 295, 606/296
See application file for complete search history.

(56) References Cited

U.S. PATENT DOCUMENTS

| | | | |
|---|---|---|---|
| 4,904,261 A | 2/1990 | Dove et al. | 623/17 |
| 4,955,908 A | 9/1990 | Frey et al. | 623/17 |
| 5,397,364 A * | 3/1995 | Kozak et al. | 623/17.11 |
| 5,861,041 A | 1/1999 | Tienboon | 623/17 |
| 6,066,175 A | 5/2000 | Henderson et al. | 623/17.11 |
| 6,241,769 B1 | 6/2001 | Nicholson et al. | 623/17.11 |
| 6,258,125 B1 | 7/2001 | Paul et al. | 623/17.11 |
| 6,413,259 B1 * | 7/2002 | Lyons et al. | 606/295 |
| 6,432,106 B1 | 8/2002 | Fraser | 606/61 |
| 6,468,311 B2 | 10/2002 | Boyd et al. | 623/17.16 |
| 6,558,424 B2 | 5/2003 | Thalgott | 623/17.16 |
| 6,579,290 B1 | 6/2003 | Hardcastle et al. | 606/61 |
| 6,635,060 B2 | 10/2003 | Hanson et al. | 606/79 |
| 6,706,067 B2 | 3/2004 | Shimp et al. | 623/17.11 |
| 6,953,477 B2 | 10/2005 | Berry | 623/17.11 |

(Continued)

FOREIGN PATENT DOCUMENTS

| EP | 1103236 | 5/2001 | A61F 2/44 |
|---|---|---|---|
| EP | 1847240 | 10/2007 | A61F 2/44 |
| WO | WO2007/098288 | 8/2007 | A61F 2/44 |

OTHER PUBLICATIONS

SynFix-LR Technique Guide, Synthes GmbH, copyright 2006.

*Primary Examiner* — Eduardo C. Robert
*Assistant Examiner* — Julianna N Harvey
(74) *Attorney, Agent, or Firm* — Winstead PC

(57) ABSTRACT

A method and apparatus is provided for use in spinal fusion procedures. A one or two piece interbody fusion device has a fusion bearing component designed to bear the axial loading from the end plates of adjacent vertebrae. An optional retention piece prevents migration of the load bearing device. One or more fasteners secure the retention device to the vertebrae above and below the load bearing device. The fasteners cause the end plates of the vertebrae to compress the end plates to the load bearing device to facilitate proper fusion. An anti-backout mechanism prevents the fasteners backing out.

6 Claims, 9 Drawing Sheets

(56) References Cited

U.S. PATENT DOCUMENTS

| | | |
|---|---|---|
| 6,972,019 B2 | 12/2005 | Michelson .................... 606/61 |
| 6,989,031 B2 | 1/2006 | Michelson ................. 623/17.11 |
| 7,018,412 B2 | 3/2006 | Ferreira et al. ............. 623/17.11 |
| 7,018,414 B2 | 3/2006 | Brau et al. ................. 623/17.11 |
| 7,018,416 B2 | 3/2006 | Hanson et al. ............. 623/17.16 |
| 7,033,394 B2 | 4/2006 | Michelson ................. 623/17.11 |
| D530,423 S | 10/2006 | Miles et al. ................. D24/155 |
| 7,125,424 B2 | 10/2006 | Banick et al. ............. 623/17.11 |
| 7,135,043 B2 | 11/2006 | Nakahara et al. .......... 623/17.11 |
| 7,172,627 B2 * | 2/2007 | Fiere et al. ................. 623/17.11 |
| 7,674,297 B2 | 3/2010 | Falahee ..................... 623/17.16 |
| 2002/0099376 A1 * | 7/2002 | Michelson .................... 606/61 |
| 2002/0138146 A1 | 9/2002 | Jackson ........................ 709/219 |
| 2002/0161445 A1 | 10/2002 | Crozet ....................... 623/17.11 |
| 2004/0034430 A1 * | 2/2004 | Falahee ...................... 623/17.16 |
| 2004/0176764 A1 * | 9/2004 | Dant ............................. 606/61 |
| 2005/0101960 A1 | 5/2005 | Fiere et al. .................... 606/72 |
| 2005/0137597 A1 * | 6/2005 | Butler et al. .................. 606/69 |
| 2005/0143819 A1 | 6/2005 | Falahee ..................... 623/17.11 |
| 2006/0085071 A1 * | 4/2006 | Lechmann et al. ........ 623/17.11 |
| 2006/0173543 A1 * | 8/2006 | Brau et al. ................. 623/17.11 |
| 2007/0250167 A1 * | 10/2007 | Bray et al. ................. 623/17.11 |
| 2008/0161925 A1 * | 7/2008 | Brittan et al. ............. 623/17.16 |
| 2008/0306596 A1 * | 12/2008 | Jones et al. ................ 623/17.16 |
| 2009/0105831 A1 | 4/2009 | Jones et al. ................ 623/17.16 |

* cited by examiner

INTERBODY FUSION DEVICE, INTEGRAL RETENTION DEVICE, AND ASSOCIATED METHODS

CROSS REFERENCE TO RELATED APPLICATIONS

This application claims priority under 35 U.S.C. §119/120 to commonly owned U.S. Provisional patent application Ser. No. 60/981,414, filed on Oct. 19, 2007, entitled "INTERBODY FUSION DEVICE AND ASSOCIATED METHODS", which is incorporated by reference herein.

FIELD OF THE INVENTION

This invention relates to the field of spinal fusion. In particular, this invention is drawn to spinal fusion devices and associated methods.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

One problem with prior art spinal fusion techniques relates to device migration. For example, prior to complete bone fusion, a fusion device may migrate from the desired position. In examples where bone screws are used, the insertion and tightening of the bone screws tends to cause device migration. Another problem with typical prior art fusion techniques is that fusion devices, or associated plates or fasteners, protrude from the spine, causing discomfort, damage, or danger to surrounding vascular or neurological tissues.

Another problem with prior art spinal fusion techniques relates to preparing the end plates of the vertebrae for fusion. Typically, a surgeon will scrape the end plates with surgical instruments (e.g., burrs, gouges, curettes, etc.), while holding adjacent end plates apart with another instrument. This procedure can be difficult and not exact. In addition, there is a danger of damaging nearby tissue while scraping the end plates.

There is therefore a need for spinal fusion devices and instruments, as well as related spinal fusion procedures, that adequately treats degenerative disc disease and other spinal conditions, while providing improvements over the prior art.

SUMMARY OF THE INVENTION

An apparatus of the invention includes a fusion bearing device and is configured to fit between two adjacent vertebrae, the fusion bearing device having one or more openings to allow access to the end plates of the two adjacent vertebrae, a retention device configured to prevent migration of the fusion bearing device, and one or more fasteners coupled to the retention device to compress the two adjacent vertebrae to the fusion bearing device.

In one embodiment, a spinal fusion device, including a fusion bearing device, is configured to fit between two adjacent vertebrae, the fusion bearing device having an open end, and a retention device configured to couple to the fusion bearing device, at least partially closing the open end.

Another embodiment of the invention provides a method of fusing adjacent vertebrae including inserting an interbody fusion device between two adjacent vertebrae, preparing the end plates of the vertebrae for fusion by accessing the end plates through one or more openings formed in the interbody fusion device, and securing a retention device to interbody fusion device to prevent migration of the interbody fusion device.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

The present invention relates to spinal fusion implants and related spinal fusion procedures for use in cervical and lumbar applications. One type of spinal fusion is interbody fusion. Typically, an interbody fusion procedure places a bone graft between the vertebra in the area normally occupied by an intervertebral disc. In preparation for a spinal fusion procedure, the intervertebral disc is removed. The end plates are then scraped to prepare the end plates for fusion. Scraping the end plates will disrupt the boney tissue, causing the tissue to bleed, heal, and fuse through the interbody fusion implant.

An interbody device may be placed between the vertebra to maintain spine alignment and disc height. Fusion then occurs between the endplates of the vertebrae. In some examples, fusion is augmented by a process called fixation, meaning the placement of screws, rods or plates to stabilize the vertebra to facilitate bone fusion. The present invention provides an interbody fusion device that overcomes problems found in the prior art.

Generally, the present invention provides a one or two piece interbody fusion device that may be used with anterior lumbar interbody fusion (ALIF). In one example, the interbody fusion device is a U-shaped load bearing device that is designed to bear the axial loading from the end plates of adjacent vertebrae. In other examples, the interbody fusion device includes a second piece used as a retention device whose function is to prevent migration of the load bearing device. One or more fasteners, such as bone screws or pegs secure the retention device to the vertebrae above and below the load bearing device. The fasteners cause the end plates of the vertebrae to compress the end plates to the load bearing device to facilitate proper fusion. If desired, the fasteners may include an anti-backout mechanism.

Figure 1:
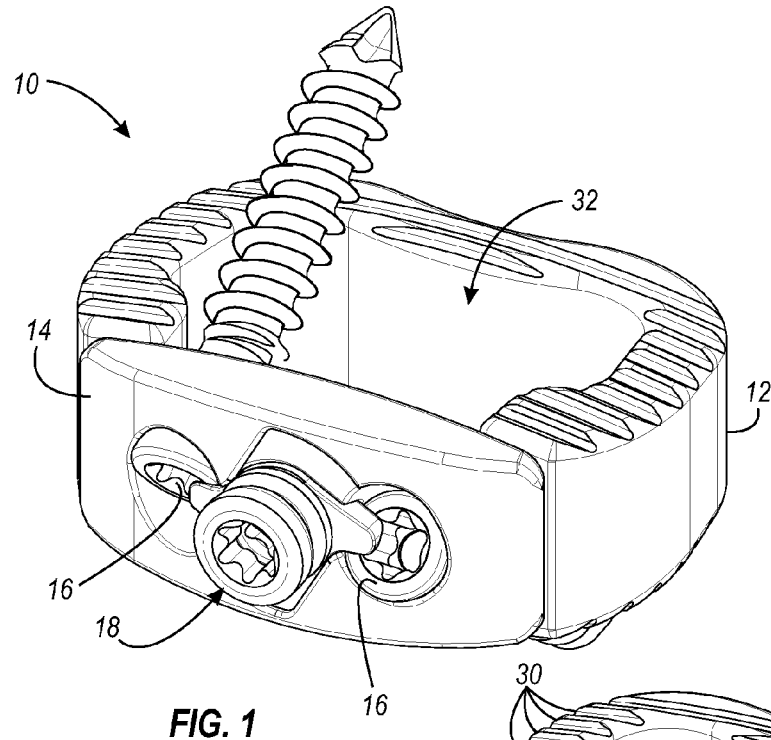
FIG. 1 is an isometric view of one example of an interbody fusion device of the present invention.

FIG. 1 is an isometric view of one example of an interbody fusion device of the present invention. FIG. 1 shows an interbody fusion device 10. The interbody fusion device 10 includes a load bearing device 12, a retention device 14, two bone screws 16, and an anti-backout mechanism 18, each of which are described in more detail below.

Figure 2:
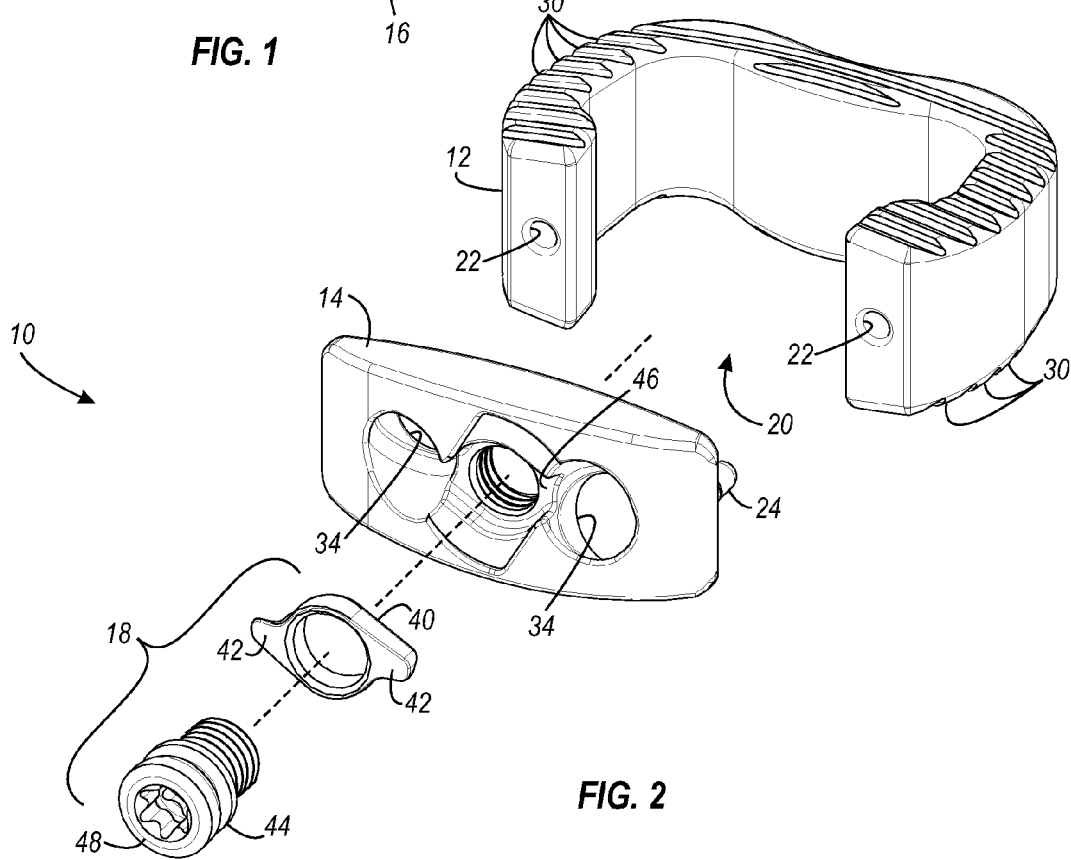
FIG. 2 is an exploded isometric diagram of the interbody fusion device shown in FIG. 1.

FIG. 2 is an exploded view of the interbody fusion device 10, showing the load bearing device 12, the retention device 14, and the anti-backout mechanism 18 separately. The load bearing device 12 is a generally U-shaped device having an open end 20. The open end defines an opening that allows access to the vertebrae end plates when the load bearing device is installed. The leading edges of the load bearing device 12 include holes 22, which are configured to receive pins 24 extending from the retention device 14. The pins 24 properly align the retention device 14 with the load bearing device 12 and hold the retention device 14 in a desired position, relative to the load bearing device 12.

The load bearing device 12 also includes a plurality of ridges 30 formed on the top and bottom ends of the device 12. The ridges 30 are angled and pointed in such a way that the ridges 30 help to hold the load bearing device 12 to the end plates of the vertebrae to reduce the chance of anterior migration of the implant. If desired, one or more openings can be formed in the load bearing device 12 to facilitate instrumentation devices (not shown).

The retention device 14 and load bearing device 12, when put together, form a hollow body 32 (FIG. 1). The hollow body 32 provides a relatively large graft volume, compared to a typical ALIF allograft. After insertion of the load bearing device 12 between adjacent vertebrae, but before placement of the retention device 14, the hollow body 32 can be filled with a prepared material that will help to facilitate fusion of the vertebrae. Examples of a material include allograft bone, bone marrow, bone morphonogenic protein (BMP), Autologous Stem Cells, etc., to facilitate fusion through opening 32.

In the example shown in FIG. 2, two holes 34 are formed in the retention device 14, and are adapted to received fasteners, such as bone screws, pegs, etc. In the example shown in FIGS. 1 and 2, one of the holes 34 is angled down, and the other hole 34 is angled up, such that a first fastener can be secured to the vertebra above the interbody fusion device 10, and a second fastener can be secured to the vertebra below the interbody fusion device 10 (described in more detail below).

FIG. 2 also illustrates the components of the anti-backout mechanism 18. The anti-backout mechanism 18 includes a locking plate 40. The plate 40 has two opposing protrusions 42 that extend outward from the plate 40. A set screw 44 is configured to extend through an opening formed in the plate 40, and thread into the retention device 14. A recess 46 is formed in the retention device 14 that is adapted to receive the locking plate 40. The set screw 44 includes a head 48 that will shear off when enough torque is applied by a driver. By shearing off the head 48, the surgeon will know that the set screw 44 is tight enough, and it will reduce the profile of the fusion device 10. The retention device 14, locking plate 40, and set screw 44 can be pre-assembled, such that a surgeon will have a single piece that is attached to the load bearing device 12. Once the bone screws are installed, the surgeon needs only to turn the set screw 44 with a driver to lock the bone screws in place. When the head 48 shears off, it will stay attached to the driver as the surgeon removes the driver from the patient. More details of the operation of the anti-backout mechanism 18 is described below.

Figure 3:
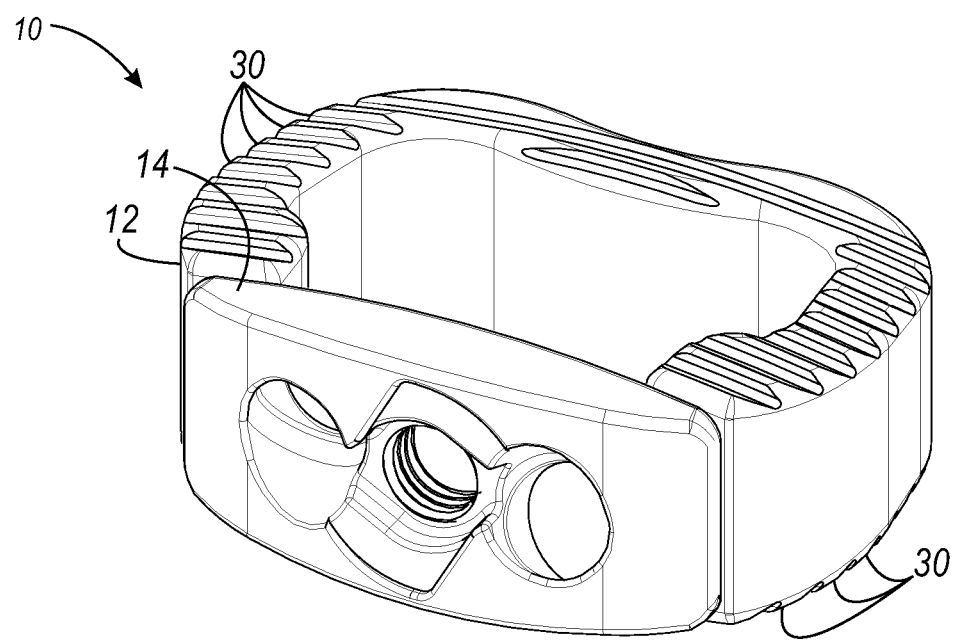
FIG. 3 is an isometric diagram of the interbody fusion device shown in FIG. 2, with the retention device assembled with the load bearing device.

FIG. 3 is an isometric diagram of the interbody fusion device 10 shown in FIG. 2 with the retention device 14 placed with the load bearing device 12. For clarity, the anti-backout mechanism is not shown in FIG. 3. As shown, the retention device 14 fits on the front edges of the load bearing device 12, with the pegs 24 inserted into the openings 22. The resulting assembly provides a load bearing structure (load bearing device 12) that is safely secured in place without any fasteners having to be placed directly into the load bearing device 12. FIG. 3 also illustrates that the height of the retention device 14 is less than the height of the load bearing device 12. As a result, all of the load on the vertebrae will be placed on the load bearing device 12, and not on the retention device 14. At the same time, the load bearing device 12 is securely is the position desired by the surgeon. In some prior art devices, the fastening mechanisms (e.g., cervical plates with screws, spacers held in place by off-set screws, etc.), will bear some of the load, increasing the likelihood of device failure or migration. In addition, with typical prior art devices, a spacer is likely to migrate or twist slightly as bone screws are tightened by the surgeon. With the interbody fusion device 10 of the present invention, the load bearing structure will remain stationary, even as bone screws are tightened to secure the retention device in place.

Figure 4:
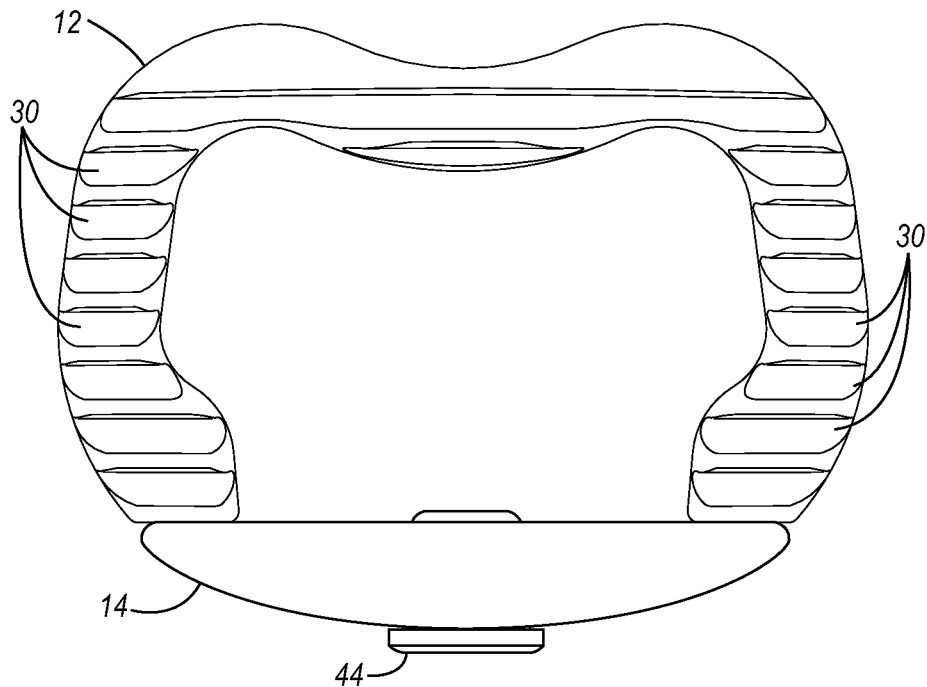
FIG. 4 is a top view of an assembled interbody fusion device shown in FIGS. 1-3.
Figure 5:
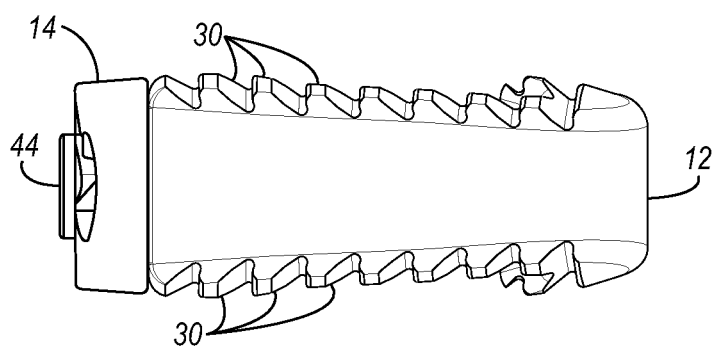
FIG. 5 is a side view of the interbody fusion device shown in FIG. 4.
Figure 6:
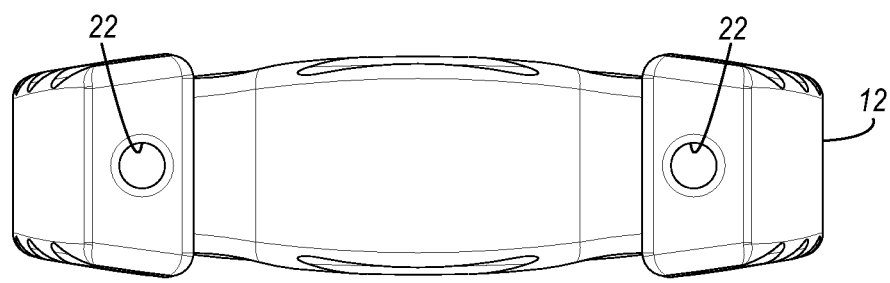
FIG. 6 is a front view of a load bearing device.

FIG. 4 is a top view of the assembled interbody fusion device 10 shown in FIGS. 1-3 (without the bone screws). 4. As shown, when the load bearing device 12 and retention device 14 are assembled together, the interbody fusion device 10 has a generally round profile, that substantially fits within a vertebral body (shown in more detail below). FIG. 5 is a side view showing the load bearing device 12 and the retention device 14. FIG. 5 also more clearly illustrates that the height of the load bearing device 12 is greater than the height of the retention device 14. As a result, the load bearing device 12 will be the structure (primarily, the ridges 30) that engages the end plates of the vertebrae, thus supporting the axial loading of the vertebrae. FIG. 5 also illustrates the slightly concave (domed) shape of the top and bottom sides of the load bearing device 12. These are the sides that will interface with the vertebrae end plates. FIG. 6 is a front view of the load bearing device 12, which, like FIG. 5, illustrates the anatomic shape of the load bearing device 12.

As described above, a interbody fusion device of the present invention is intended to be installed between the end plates of two adjacent vertebrae to facilitate the fusion of the vertebrae. FIGS. 7-11 further illustrate the installation of an interbody fusion device of the present invention between adjacent vertebrae.

Figure 7:
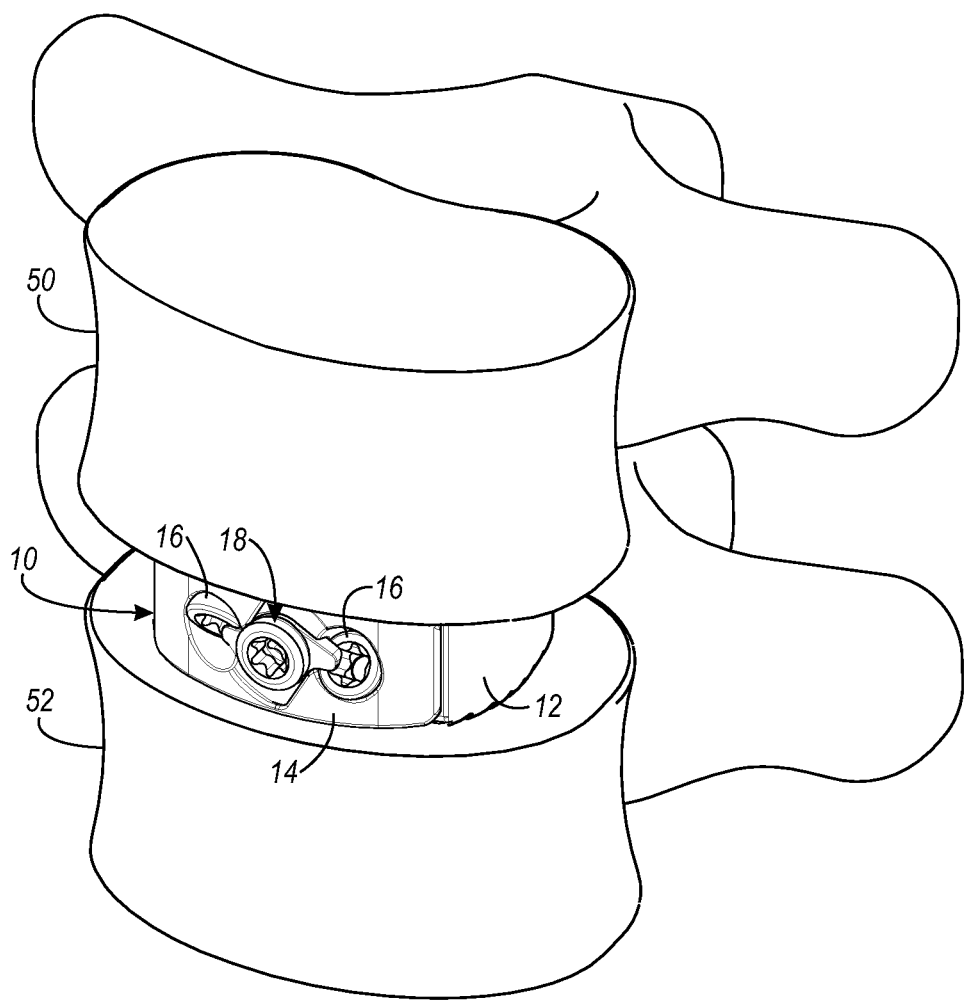
FIG. 7 is an isometric diagram of the interbody fusion device shown in FIG. 1 installed between the end plates of two adjacent vertebrae.

FIG. 7 is an isometric diagram of the interbody fusion device 10 shown in FIG. 1 installed between the end plates of two adjacent vertebrae 50 and 52 to facilitate the fusion of the vertebrae 50 and 52. The interbody fusion device 10 provides load bearing support as well as the proper spacing between the vertebrae 50 and 52 while fusion of the vertebrae takes place. As described in more detail below, the interbody fusion device 10 is positioned between the end plates of the vertebrae 50 and 52 within the vertebral body in the area usually occupied by the intervertebral disc. For clarity, the disc annulus is not shown, so the position of the load supporting device 12 can be seen.

Figure 8:
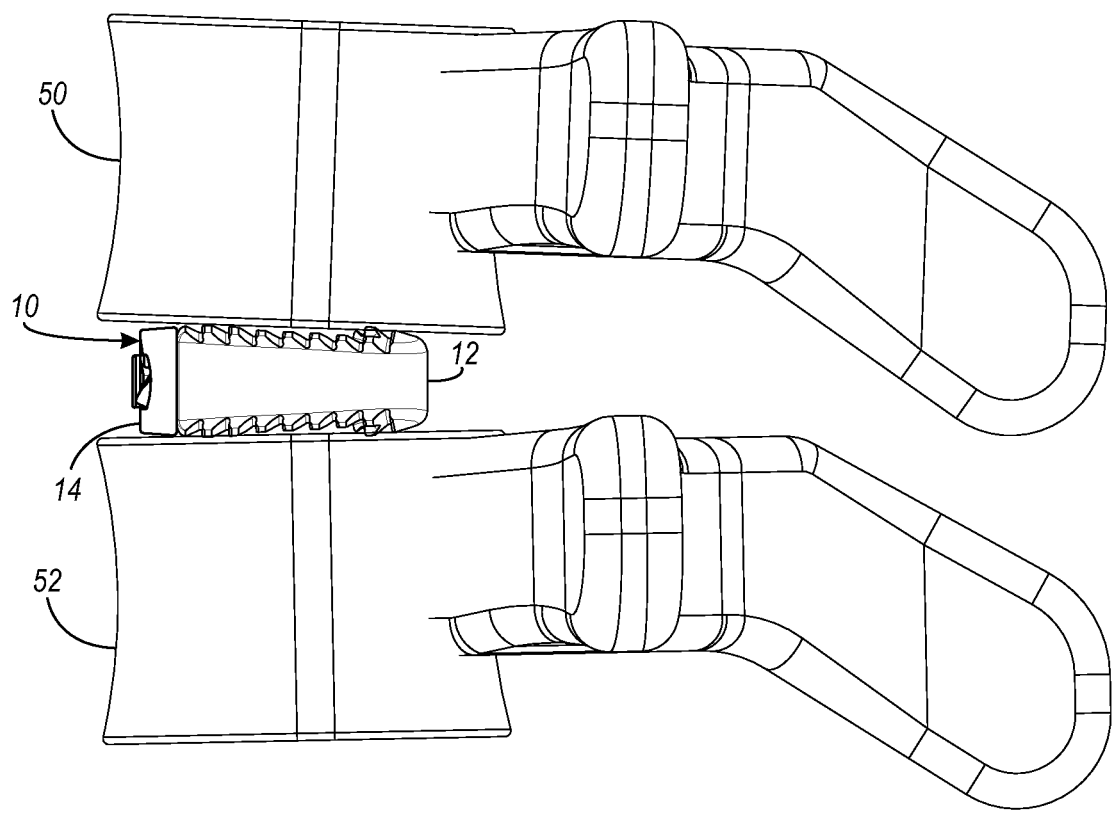
FIG. 8 is a side view of the interbody fusion device shown in FIG. 7.

FIGS. 8-11 further illustrate the installation of an interbody fusion device of the present invention between adjacent vertebrae. FIG. 8 is a side view of the interbody fusion device 10. As shown in FIG. 8, the interbody fusion device 10 has a zero-profile anteriorly. In other words, the interbody fusion device 10 has a shape (e.g., see FIG. 4) in the axial plane that substantially fits within the perimeter defined by the vertebrae. In typical prior art devices, a cervical plate, or similar structure, is affixed to the side of the vertebrae, creating an extending profile that can cause discomfort, or damage to nearby tissue. Also note from FIG. 8 that the interbody fusion device 10 (not including the bone screws 16) also does not extend beyond (above or below) the end plates of the vertebrae.

Figure 9:
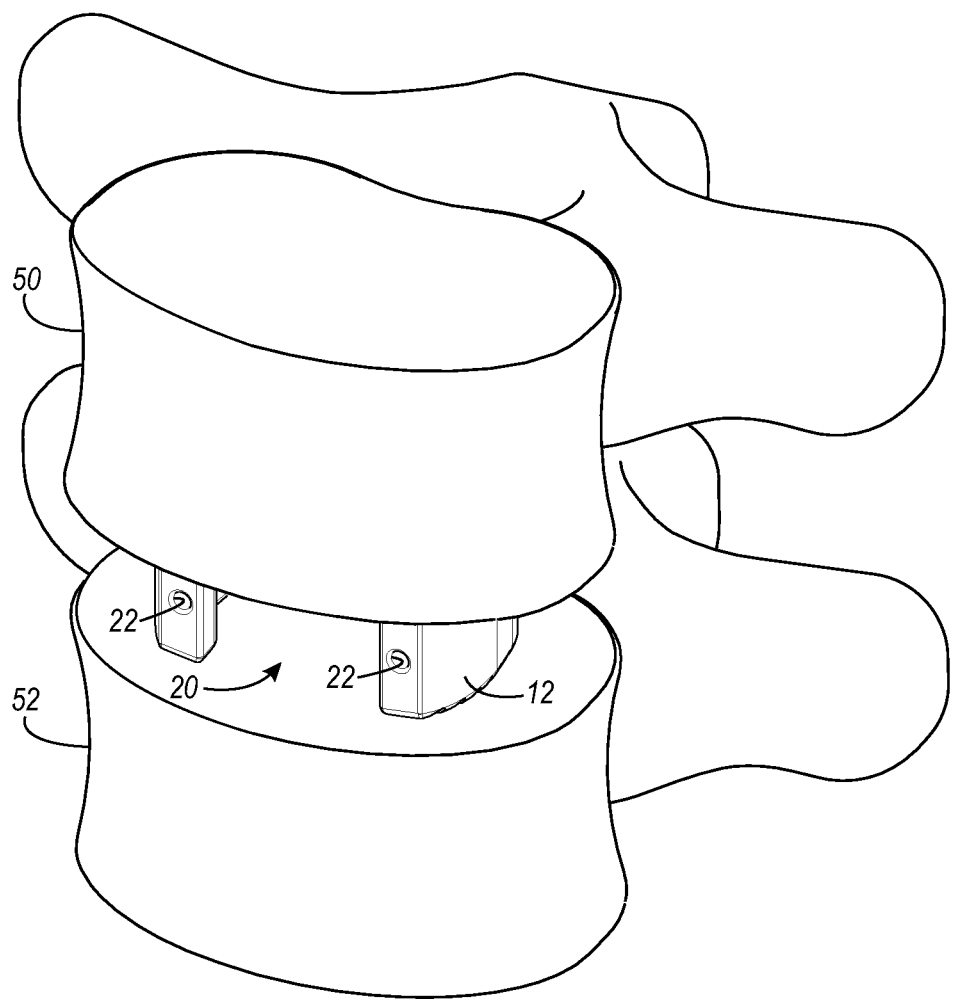
FIG. 9 is an isometric view of a load bearing device inserted between two adjacent vertebrae.
Figure 10:
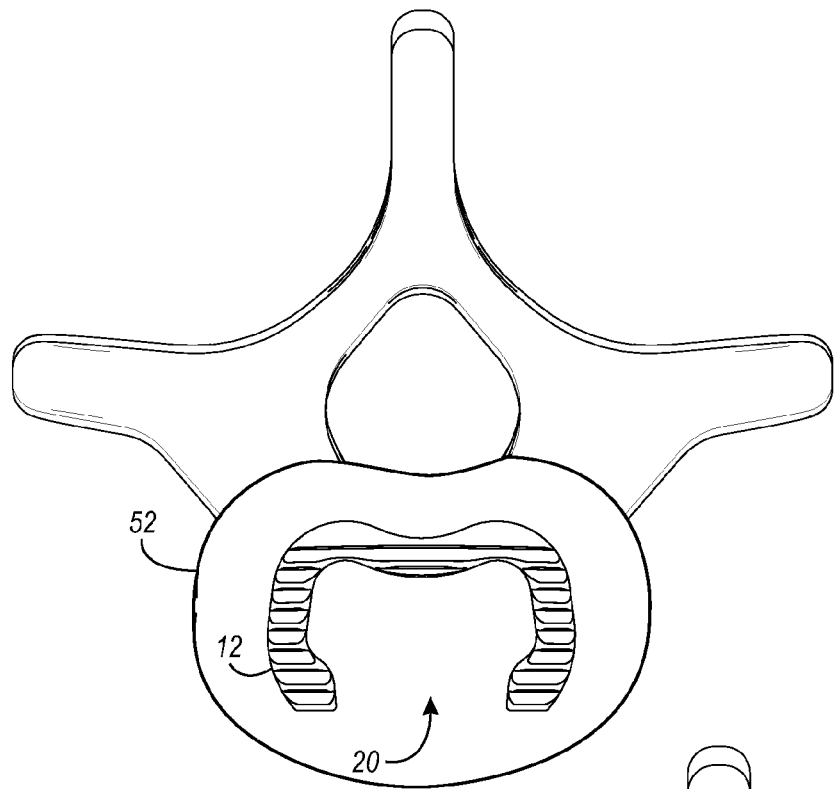
FIG. 10 is a top view of the load bearing device shown in FIG. 9.

Prior to the insertion of the interbody fusion device 10, the intervertebral disc is removed, so the interbody fusion device 10 can be placed between the vertebrae 50 and 52. In one example, a window is cut in the disc annulus. Next, portions of the nucleus pulposus are removed so that the interbody fusion device 10 can fit between the vertebrae 50 and 52 as shown in the figures. FIG. 9 is an isometric view of the load bearing device 12 of the interbody fusion device 10 inserted between two adjacent vertebrae 50 and 52, but prior to the installation of the retention device 14. Again, the annulus is not shown, for clarity. FIG. 10 is a top view of the load bearing device 12 shown in FIG. 9, with the vertebrae 50 not shown.

Figure 11:
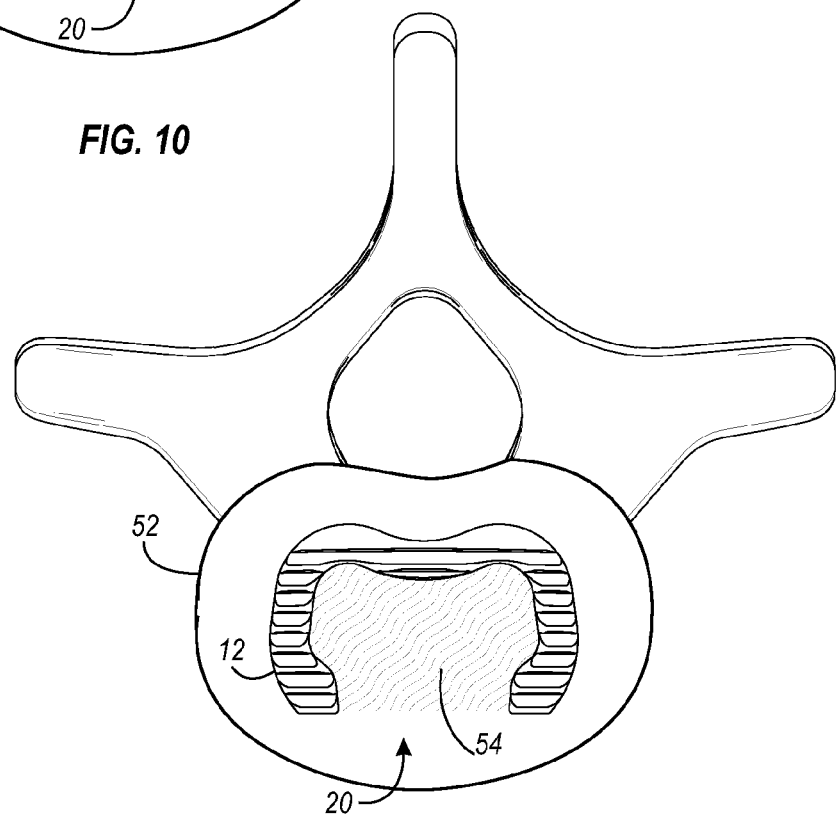
FIG. 11 is a top view of the load bearing device shown in FIG. 9, including the fusion material.

As FIGS. 9 and 10 illustrate, an open end 20 of the load bearing device 12 provides the surgeon with access to the end plates of the vertebrae 50 and 52 in the fusion region. Once the load bearing device 12 is inserted between the vertebrae 50 and 52, the surgeon can use an instrument to scrape the endplates of the vertebrae 50 and 52 within the area defined by the device 12. Preparing the end plates while the device 12 is in place has several advantages. First, the surgeon will not have to use another instrument to hold the vertebrae apart during the preparation process. Also, the surgeon can scrape the endplates more quickly and aggressively, since the preparation instrument is confined by the device 12. Once the surgeon has prepared the end plates, a desired material 60 can be placed between the endplates through the opening 20. The material can any desired material that will help to facilitate fusion of the vertebrae, for example, allograft bone, bone marrow, bone morphonogenic protein (BMP), Autologous Stem Cells, etc. FIG. 11 shows material 60 (the shaded area) placed between the endplates and within the device 12.

Following is an example of how a interbody fusion device of the present invention may be used in an ALIF spinal fusion procedure. As described above, a window is cut in the anterior side of the disc annulus to allow an interbody fusion device to be inserted. Next, the nucleus pulposus is cleaned out to provide room for the interbody fusion device. Next, a load bearing device 12 of the desired size (e.g., having a height to get the desired spacing between the vertebrae) is inserted between the end plates of the adjacent vertebrae using the appropriate instrumentation. Once the surgeon is satisfied that the load bearing device is in the desired position, the end plates can be prepared using the appropriate instruments (e.g., burrs, gouges, curettes, etc.). Next, the space between the endplates and within the load bearing device can be filled with a material that will help to facilitate fusion. Next, the retention device 14 coupled to the load bearing device 12, while aligning the pegs 24 with the holes 22. Note that, because the height of the retention device is less than the height of the load bearing device, the retention device 14 be put in place without interfering with the relative placement of the load bearing device 12 and the end plates of the adjacent vertebrae. Also, the retention device 14 is stress shielded and is not axial loaded by the vertebrae. Once the retention device is in place, the bone screws 16 can be installed through the openings 34 and into the vertebrae. As the bone screws 16 are tightened, the vertebrae will compress vertebral bodies 50 and 52 onto the load bearing member 12, which will help facilitate fusion. Also, since the bone screws 16 secure the retention device 14, and do not directly secure the load bearing device 12, the bone screws will not tend to cause the interbody fusion device 10 to migrate. Next, the anti-backout mechanism 18 is used to prevent the bone screws 16 from loosening. As is described in detail below, the surgeon can turn the set screw 44 with driver until the head 48 sheers off. The protrusions 42 of the locking plate 40 will then be positioned over the ends of the bone screws 16, preventing the screws 16 from backing out.

The interbody fusion device of the present invention can be made from any desired materials. In one example, the load bearing device is made from PEEK® (or a similar material), bone, metal, or any other structural substitute. In one example, the retention device is made from PEEK® (or a similar material), bone, metal, or any other structural substitute. If the components of the interbody fusion device are radio-lucent (such as with PEEK®), then doctors will be able monitor the fusion process better with X-rays. If desired, one or more radio opaque markers can be embedded into the interbody fusion device, which will show up in an X-ray. Since the positions of the markers are known relative to the fusion device, a doctor can determine the position of the fusion device in an X-ray by viewing the positions of the markers.

An interbody fusion device of the present invention may be configured to any desired size or shape. In one example, load bearing devices can be provided in multiple thicknesses, allowing a surgeon to select a desired size (e.g., 10.5 mm, 12.5 mm, 14.5 mm, 16.5 mm, 18.5 mm, etc.). In the examples shown in the figures, the load bearing device has about 6° of lordosis (e.g., see FIG. 5). Of course any desired angle could be used.

Figure 12:
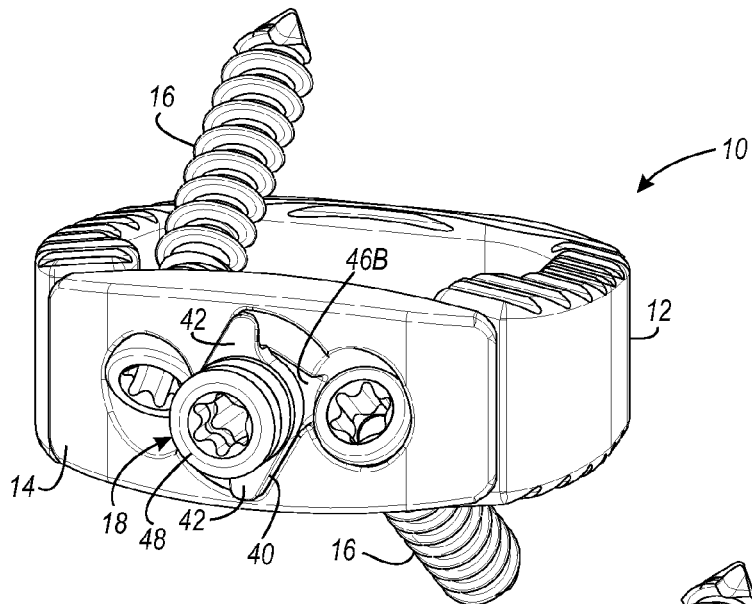
FIGS. 12-14 are isometric view illustrating the operation of an anti-backout mechanism.
Figure 13:
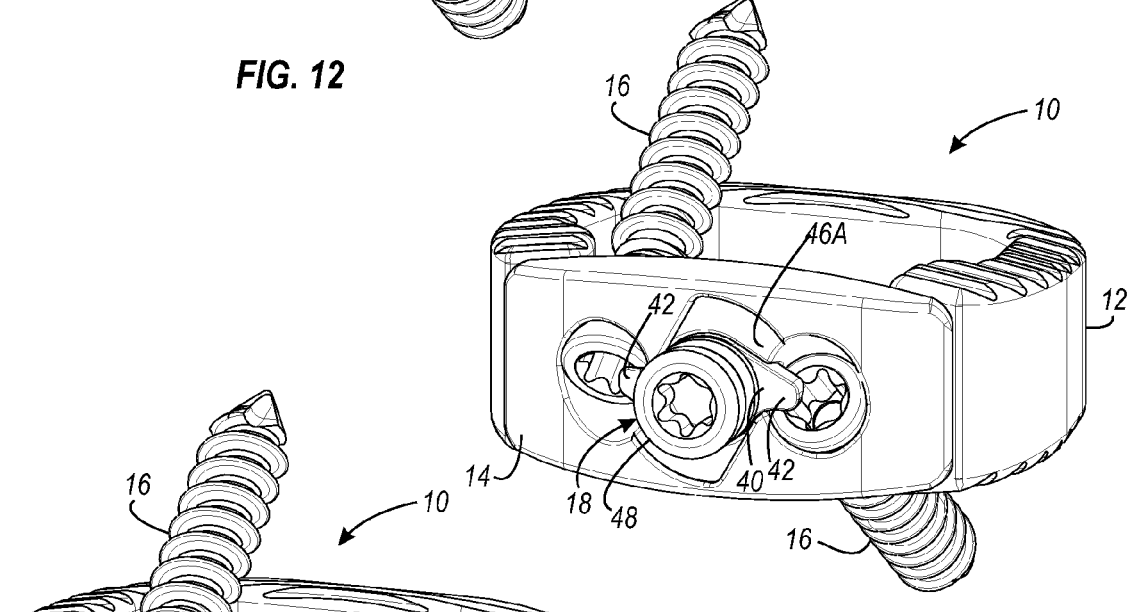
Figure 14:
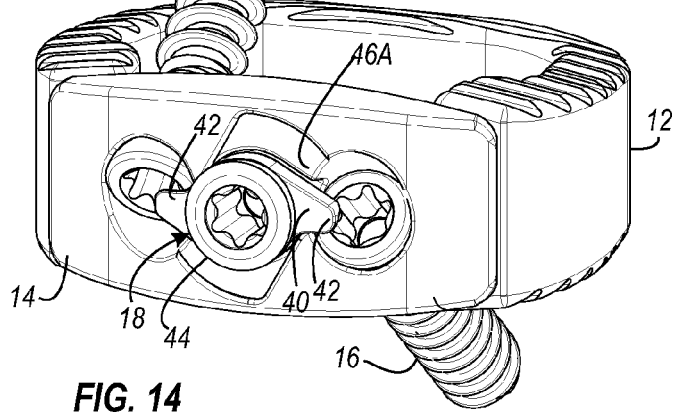

FIGS. 12-14 are isometric view illustrating the operation of the anti-backout mechanism described above. FIG. 12 shows the interbody fusion device 10 after the bone screws have been installed. Note that the position of the protrusions 42 of the locking plate 40 are such that the openings 34 are not obstructed, allowing a surgeon to install the bone screws 16. As mentioned above, the retention device 14 can come pre-assembled with the anti-backout mechanism in the position shown in FIG. 12. One the bone screws are in place, the surgeon can use a driver to turn the set screw 44. FIG. 13 shows the interbody fusion device 10 after the set screw 44 has been turned. In this example, the set screw turned about 90 degrees until the protrusions 42 obstruct the heads of the bone screws 16. When the locking plate 40 is in this position, the bone screws can not come out. As shown in FIGS. 12 and 13, the recess 46 has multiple depths. In this example, the recess has a first depth (shown at 46A) and a second deeper depth shown at 46B. As the locking plate 40 is turned, the locking plate will drop from the recess 46A and seat into the deeper recess 46B. When the locking plate 40 is seated within the deeper recess 46B (FIGS. 13 and 14), the shape of the recess 46 will tend to prevent the locking plate 40 from turning the other way. When the surgeon applies the appropriate amount of torque to the set screw 44, the head 48 of the set screw 44 will sheer off, eliminating the need for a torque wrench. This also lessens the profile of the implant (see FIG. 8). If the implant has to be removed in the future, a surgeon can use a driver and loosen the set screw 44 until the protrusions 42 no longer obstruct the bone screws 16.

Figure 15A:
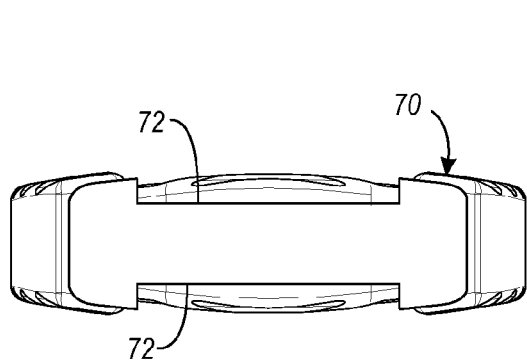
FIGS. 15-17 illustrate other configurations of interbody fusion devices.
Figure 15B:
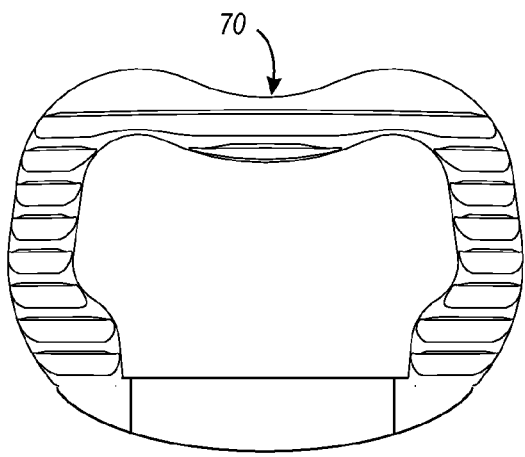

The interbody fusion device described above can be configured in any desired manner. FIGS. 15-17 illustrate other examples of interbody fusion devices. FIG. 15A is a front view of a load bearing device 70. FIG. 15B is a top view of the load bearing device 70 shown in FIG. 15A. In this example, the load bearing device 70 does not have a completely open front end, which increases its strength. Two openings 72 are formed near the top and bottom surfaces of the load bearing device 70, which provides a way for a surgeon to prepare the end plates of the vertebrae after the device 70 is installed. In this example, end plate preparation instruments can be provided that fit through the openings 72. The openings 72 are also used to allow the surgeon to pack the space between the end plates with a desired fusion material.

Figure 16A:
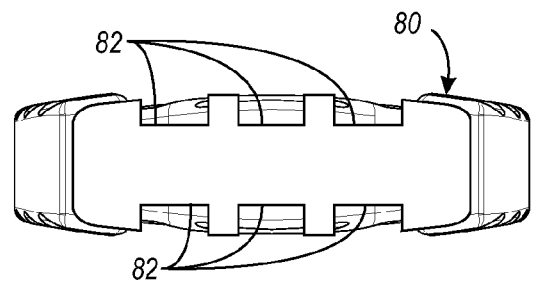
Figure 16B:
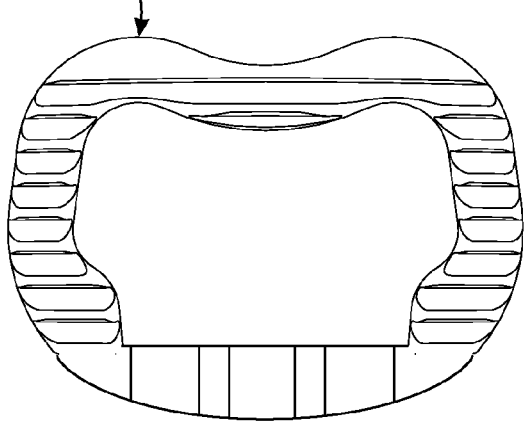

FIG. 16A is a front view of a load bearing device 80. FIG. 16B is a top view of the load bearing device 80 shown in FIG. 16A. In this example, the load bearing device 80 does not have a completely open front end, which increases its strength. Six openings 82 are formed near the top and bottom surfaces of the load bearing device 80, which provides a way for a surgeon to prepare the end plates of the vertebrae after the device 80 is installed. In this example, end plate preparation instruments can be provided that fit through the openings 82. The openings 82 are also used to allow the surgeon to pack the space between the end plates with a desired fusion material.

Figure 17A:
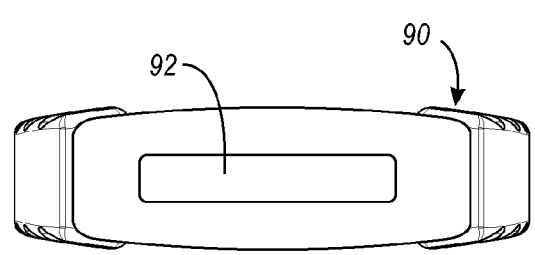
Figure 17B:
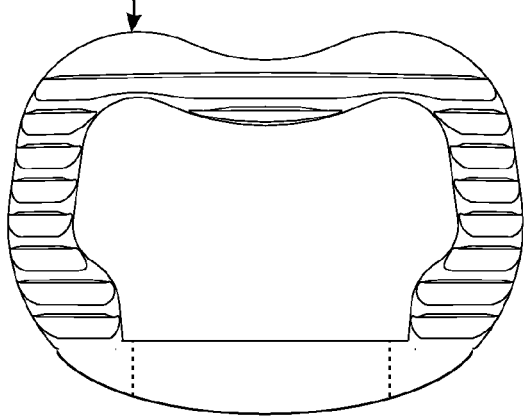

FIG. 17A is a front view of a load bearing device 90. FIG. 17B is a top view of the load bearing device 90 shown in FIG. 17A. In this example, the load bearing device 90 does not have a completely open front end, which increases its strength. In this example, an opening 92 is formed near the center of the load bearing device 80, which allows the surgeon to pack the space between the end plates with a desired fusion material. To prepare the end plates, a thin preparation tool can be inserted between the end plates the corresponding the top or bottom surface of the device 90. Numerous other configurations of fusion devices are also possible.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A spinal fusion device comprising:
   a single piece U-shaped load bearing device configured to fit between two adjacent vertebrae, the load bearing device having one or more openings to allow access to surgically prepare the end plates of the two adjacent vertebrae after insertion of the load bearing device between the two adjacent vertebrae;
   a stress shielded, separate retention device configured to prevent migration of the load bearing device, wherein the height of the retention device is less than the load bearing device, wherein the retention device does not contact the end plates of the vertebrae;
   one or more fasteners coupled to the stress shielded, separate retention device to compress the two adjacent vertebrae to the load bearing device wherein the one or more fasteners do not pass through the load bearing device; and
   wherein the spinal fusion device has a shape that is zero-profile anteriorly; and
   further comprising an anti-backout mechanism coupled to the retention device, wherein the anti-backout mechanism comprises a locking plate and said locking plate comprises at least two opposing protrusions that extend outward from the plate and are positioned over the ends of the one or more fasteners and prevent the one or more fasteners from backing out, and further wherein the locking plate is located within a recess in the retention device and wherein a portion of the recess has a first depth and a portion of the recess has a second depth and wherein the second depth is deeper than the first depth and the locking plate has a locked position and an unlocked position, wherein, in the unlocked position, the locking plate is disposed within the first depth of the recess and in the locked position, the locking plate is disposed within the second depth of the recess.

2. The spinal fusion device of claim 1, wherein the one or more fasteners are bone screws.

3. The spinal fusion device of claim 1, wherein each of the one or more fasteners are inserted through an aperture formed in the retention device.

4. The spinal fusion device of claim 1, wherein the one or more openings in the load bearing device are adapted for receiving a fusion enhancing material.

5. The spinal fusion device of claim 1, wherein the one or more openings in the U-shaped load bearing device are formed on the anterior side of the load bearing device.

6. The spinal fusion device of claim 1, further comprising one or more pegs extending from the retention device, and corresponding holes formed in the U-shaped load bearing device for aligning the retention device with the U-shaped load bearing device.

* * * * *